US011534190B2

(12) United States Patent
Chu

(10) Patent No.: US 11,534,190 B2
(45) Date of Patent: *Dec. 27, 2022

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 16/786,336

(22) Filed: Feb. 10, 2020

(65) Prior Publication Data
US 2020/0178990 A1 Jun. 11, 2020

Related U.S. Application Data

(63) Continuation of application No. 15/498,998, filed on Apr. 27, 2017, now Pat. No. 10,588,650.
(Continued)

(51) Int. Cl.
*A61B 17/221* (2006.01)
*A61B 17/3207* (2006.01)
(Continued)

(52) U.S. Cl.
CPC ...... *A61B 17/221* (2013.01); *A61B 17/00234* (2013.01); *A61B 17/22* (2013.01);
(Continued)

(58) Field of Classification Search
CPC .. A61B 2017/0034; A61B 2017/22072; A61B 2017/0042; A61B 2017/2215;
(Continued)

(56) References Cited

U.S. PATENT DOCUMENTS 5,312,418 A 5/1994 Bonnet
5,370,647 A * 12/1994 Graber ............. A61B 17/00234
606/127
(Continued)

FOREIGN PATENT DOCUMENTS

CN 1051498 A 5/1991
CN 101484203 A 7/2009
(Continued)

OTHER PUBLICATIONS

International Search Report and Written Opinion for International Application No. PCT/US2017/029824, dated Jun. 9, 2017 (14 pages).
(Continued)

*Primary Examiner* — Jocelin C Tanner
(74) *Attorney, Agent, or Firm* — Bookoff McAndrews, PLLC

(57) ABSTRACT

A medical system may include an insertion device having a handle, a shaft coupled to the handle of the insertion device, and a port positioned on the handle of the insertion device. The port may be in fluid communication with a working channel of the shaft. The port may be a female luer port. The medical system may further include a medical device having a control member terminating in an end effector, a handle having a plurality of circumferential slots along the length of the handle, and a plunger moveable along a longitudinal axis of the handle of the medical device between a first position and a second position. In the first position, the end effector may be positioned within the shaft, and in the second position, the end effector may be positioned distally of the shaft.

20 Claims, 3 Drawing Sheets

Related U.S. Application Data

(60) Provisional application No. 62/332,682, filed on May 6, 2016.

(51) Int. Cl.
    *A61B 17/22*     (2006.01)
    *A61B 17/29*     (2006.01)
    *A61B 17/00*     (2006.01)

(52) U.S. Cl.
    CPC ...... *A61B 17/2909* (2013.01); *A61B 17/3207* (2013.01); *A61B 2017/00296* (2013.01); *A61B 2017/00318* (2013.01); *A61B 2017/00367* (2013.01); *A61B 2017/00477* (2013.01); *A61B 2017/2215* (2013.01); *A61B 2017/22079* (2013.01); *A61B 2217/005* (2013.01); *A61B 2217/007* (2013.01)

(58) Field of Classification Search
    CPC ........... A61B 2017/22079; A61B 2017/00477; A61B 2017/00367; A61B 2017/00318; A61B 2017/00296; A61B 1/018; A61B 1/015; A61B 1/00133; A61B 1/00128; A61B 1/00087; A61B 1/00066; A61B 2217/007; A61B 2217/005; A61B 17/3207; A61B 17/2909; A61B 17/22; A61B 17/00234; A61B 17/221
    See application file for complete search history.

(56) References Cited

U.S. PATENT DOCUMENTS

| | | | |
|---|---|---|---|
| 5,893,869 A | | 4/1999 | Barnhart et al. |
| 6,019,743 A | * | 2/2000 | Cole ................ A61F 13/26 604/15 |
| 6,045,526 A | * | 4/2000 | Jackson ............ A61F 13/26 604/15 |
| 6,419,679 B1 | | 7/2002 | Dhindsa |
| 10,588,650 B2 | * | 3/2020 | Chu .................. A61B 17/2909 |
| 2004/0097831 A1 | | 5/2004 | Bourne et al. |
| 2004/0236213 A1 | * | 11/2004 | Jones ................ A61B 90/39 600/431 |
| 2006/0116692 A1 | | 6/2006 | Ward |
| 2006/0184090 A1 | * | 8/2006 | Davis ................ A61M 31/007 604/19 |
| 2006/0224041 A1 | * | 10/2006 | Okada ............... A61B 1/012 600/106 |
| 2006/0247495 A1 | * | 11/2006 | Bacher .............. A61B 17/29 600/105 |
| 2010/0331900 A1 | * | 12/2010 | Garabedian ...... A61B 17/00234 606/86 A |
| 2011/0015674 A1 | | 1/2011 | Howard et al. |
| 2011/0282382 A1 | * | 11/2011 | McAlister ........ A61M 5/19 606/213 |
| 2012/0158021 A1 | | 6/2012 | Morrill |
| 2014/0171735 A1 | * | 6/2014 | Galperin .......... A61B 17/2909 606/127 |
| 2014/0200402 A1 | | 7/2014 | Snoke et al. |
| 2014/0257253 A1 | * | 9/2014 | Jemison ........... A61B 1/00133 606/1 |
| 2016/0089127 A1 | | 3/2016 | Kirkemo |
| 2016/0096005 A1 | | 4/2016 | Bhola |
| 2016/0331468 A1 | * | 11/2016 | Lee .................. A61B 90/37 |

FOREIGN PATENT DOCUMENTS

| | | |
|---|---|---|
| CN | 103370019 A | 10/2013 |
| EP | 0573273 A3 | 3/1994 |
| EP | 0 543 499 B1 | 4/1996 |

OTHER PUBLICATIONS

Chinese Office Action in corresponding Chinese Application No. 201780026446.3, dated Nov. 11, 2020 (18 pages).

\* cited by examiner

MEDICAL SYSTEMS, DEVICES, AND RELATED METHODS

CROSS-REFERENCE TO RELATED APPLICATIONS

This patent application is a continuation of and claims the benefit of priority to U.S. Non-Provisional patent application Ser. No. 15/498,998, filed Apr. 27, 2017, which claims the benefit of priority to U.S. Provisional Patent Application No. 62/332,682, filed May 6, 2016, the entireties of which is incorporated herein by reference.

TECHNICAL FIELD

Various aspects of the present disclosure relate generally to medical systems, devices, and related methods. More specifically, the present disclosure relates to devices, systems, and methods for retrieving objects and/or performing therapies within a subject.

BACKGROUND

Medical devices, such as baskets, are often used to remove organic material (e.g., blood clots, tissue, and biological concretions such as urinary, biliary, and pancreatic stones) and inorganic material (e.g., components of a medical device or other foreign matter), which may obstruct or otherwise be present within a subject's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Medical devices are also used in lithotripsy and ureteroscopy procedures to treat urinary calculi (e.g., kidney stones) in the ureter of a subject.

Such medical devices may be passed through a working channel of a suitable insertion device (such as, e.g., an endoscope, ureteroscope, laparoscope, etc.) positioned in a body cavity in order to reach an operative site at a distal end of the insertion device. Typically, such procedures require two or more operators: one operator to hold the insertion device, and another operator to move the medical device. If multiple medical devices are deployed, then even more operators may be required. Using more than one operator increases both the cost and complexity of the medical procedure as each additional operator may add incremental cost, and the operators must carefully coordinate their movements in order to complete a procedure.

The systems, devices, and methods of the current disclosure may rectify some of the deficiencies described above or address other aspects of the prior art.

SUMMARY

Examples of the present disclosure relate to, among other things, medical retrieval devices. Each of the examples disclosed herein may include one or more of the features described in connection with any of the other disclosed examples.

In one example, a medical system may include an insertion device having a handle, a shaft coupled to the handle of the insertion device, and a port positioned on the handle of the insertion device. The port may be in fluid communication with a working channel of the shaft. The port may be a female luer port. The medical system may further include a medical device having a control member terminating in an end effector, a handle having a plurality of circumferential slots along the length of the handle, and a plunger moveable along a longitudinal axis of the handle of the medical device between a first position and a second position. In the first position, the end effector may be positioned within the shaft, and in the second position, the end effector may be positioned distally of the shaft.

Examples of the medical system may additionally and/or alternatively include one or more of the following features. The port may be a T-shaped or Y-shaped port having a first branch and a second branch. An adaptor may be coupled to the port, and may include a supplemental line terminating in a stop-cock. A tapered introducer, a distal end of which being positioned within the adaptor. The adaptor may comprise a male luer. The handle of the insertion device may include a clip on a proximal end thereof, the clip may include a plurality of arms defining a receiving space therebetween. The plunger may be rotatable about the longitudinal axis of the handle of the medical device. The handle of the medical device may include a channel extending along the longitudinal axis. A distal end of the plunger may be slidably positioned within a portion of the channel. A spring may be positioned within the channel. The plunger may include a knob at a proximal end thereof. The plunger may include a plurality of indicia. The circumferential slots may extend along the entire length of the handle of the medical device between the proximal end and the distal end of the handle of the medical device. A distal end of the medical device may include a male luer port. The medical device may further include a sheath coupled to the male luer port of the handle of the medical device.

In another example, a medical system may include an insertion device having a handle, a shaft coupled to the handle of the insertion device, and a clip positioned along a proximal end of the handle of the insertion device. The clip may include a plurality of arms extending from the handle of the insertion device. The insertion device may also include a port positioned on the handle of the insertion device in fluid communication with a working channel of the shaft. The port may comprise a female luer port. The medical system may also include a medical device having a control member terminating in an end effector, a handle positioned within a receiving space between the plurality of arms of the clip, and a plunger moveable along a longitudinal axis of the handle of the medical device between a first position and a second position. In the first position, the end effector may be positioned within the shaft, and in the second position, the end effector may be positioned distally of the shaft.

Examples of the medical system may additionally and/or alternatively include one or more of the following features. The handle of the medical device may include a channel extending along the longitudinal axis, a distal end of the plunger may be slidably positioned within a portion of the channel. The distal end of the plunger may be rotatable with respect to the portion of the channel about the longitudinal axis of the handle of the medical device. The plunger may include a plurality of indicia. A spring positioned within the channel. The handle of the medical device may include a plurality of circumferential slots.

In another example, a method for treating a patient may include positioning an insertion device relative to a location within a patient and delivering a medical device through a female luer port and working channel of insertion device. The method may also include clipping a handle of the medical device to a handle of the insertion device via a clip on the handle of the insertion device and simultaneously holding the handle of the insertion device and the handle of the medical device with a single hand. Additionally, the method may include axially advancing a plunger of the medical device with a digit of the hand and extending an end effector of the medical device distally of the working channel of the insertion device.

Examples of the method may additionally and/or alternatively include one or more of the following features. Rotating the plunger of the medical device and rotating the end effector of the medical device. Axially advancing the plunger and rotating the plunger simultaneously via the digit of the hand. Bending the handle of the medical device.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems and devices for diagnosing and/or treating internal areas of a subject's body. The medical system may include an insertion device and one or medical devices operably coupled thereto for introduction of an end effector through the insertion device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figures 1, 1A:
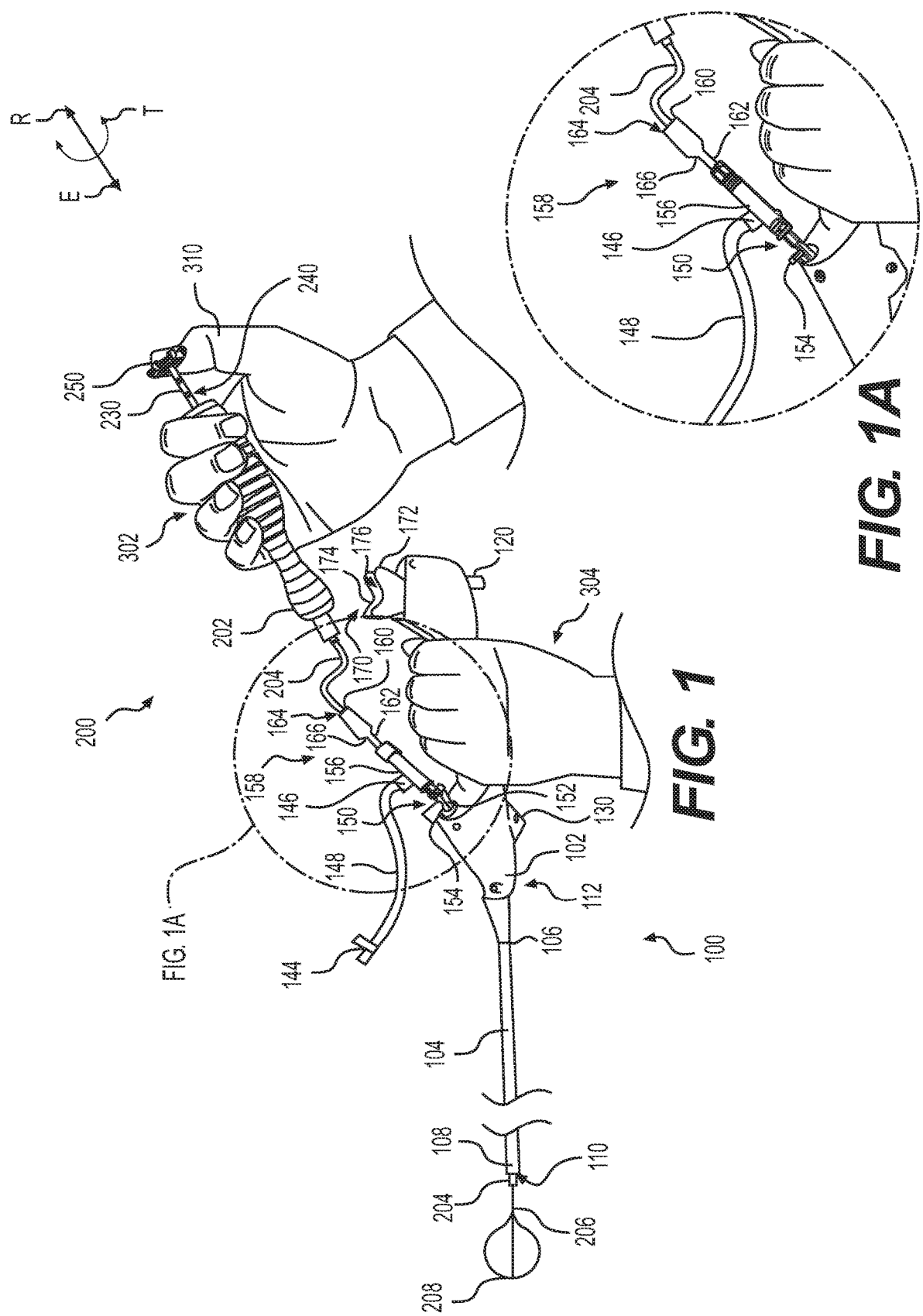
FIG. 1 illustrates an exemplary medical system having an exemplary insertion device and an exemplary medical device arranged for operation by a single operator.
FIG. 1A illustrates an enlarged view of a portion of the medical system of FIG. 1.

FIG. 1 illustrates an exemplary medical system 100 comprising a handle 102 coupled to shaft 104. Insertion device 100 may include any device configured to allow an operator to perform medical diagnoses and/or treatments on a subject. For example, insertion device 100 may include any device configured to allow a user to access and view internal areas of a subject's body. Additionally or alternatively, insertion device 100 may itself be a medical device and/or include any device configured to deliver one or more medical devices 200, such as, for example, biopsy forceps, graspers, baskets, snares, probes, scissors, retrieval devices, lasers, and/or other tools, into a subject's body. Insertion device 100 may be inserted into one of a variety of body openings, lumens, and/or cavities. For example, insertion device 100 may be inserted into any portion of a urinary tract, such as a ureter, a gastrointestinal lumen, such as an esophagus, a vascular lumen, and/or an airway.

According to aspects of the present disclosure, insertion device 100 may be a ureteroscope. In some contemplated examples, insertion device 100 may be a sterile, single-use, and disposable ureteroscope. Alternatively, insertion device 100 may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable.

Handle 102 of insertion device 100 may have any shape suitable for gripping and controlling insertion device 100. For example, handle 102 may have an ergonomic shape designed to be held comfortably in the hand, e.g., the palm of the left hand 304. Shaft 104 may extend from a proximal end 106 to a distal end 108, such that proximal end 106 of shaft 104 may be coupled to (e.g., detachably or permanently connected to) a distal end 112 of handle 102. Insertion device 100 may include a steering mechanism for deflecting shaft 104 along one or more planes. For example, handle 102 may include an actuator 120 coupled to one or more portions of shaft 104 at or near distal end 108 via one or more control members, such as steering wires (not shown). Any suitable steering mechanism and/or actuators may be used.

Shaft 104 may include at least one working channel 110 extending between proximal end 106 and distal end 108 of shaft 104. While only a single working channel 110 is depicted, such a depiction is merely exemplary. For example, working channel 110 may be a primary working channel 110 for delivery of one or more medical devices 200, as will be described in further detail below. Shaft 104 may, however, include additional channels (not shown) extending between proximal end 106 and distal end 108 of shaft 104. Such additional channels may have different shapes and/or sizes. In some examples, shaft 104 may include one or more electronic components, such as a camera or other imaging device, a light source, and/or other sensor (not shown). Additionally or alternatively, one of the additional channels may provide a lumen for light delivery and/or steering control members (not shown) associated with actuator 120 for steering shaft 104.

Handle 102 may also include an umbilicus hub or connector 130 for facilitating electrical connections and functions, such as transferring data and/or powering a light source. In addition, as shown in FIG. 1 and FIG. 1A, handle 102 may include at least one port coupling 150 (e.g., a T-shaped or Y-shaped female luer port connection). Port coupling 150 may include a first branch 154. First branch 154 may be fluidly coupled to one or more sources of irrigation and/or suction fluid. Accordingly, irrigation fluid (not shown) may be delivered (e.g., pumped) through working channel 110, via first branch 154 to provide lubrication and/or aid in visualization. Port coupling 150 may also include a second branch 152 in communication with working channel 110, e.g., to allow for the insertion of one or more medical device(s) 200 through working channel 110 to distal end 108 of shaft 104. For example, second branch 152 may comprise a female medical (e.g., threaded) or slip luer port. The second branch 152 may be coupled to an adaptor 156 through which an end effector 208, control member 206, and/or sheath 204 of medical device 200 may be delivered into second branch 152 and working channel 110. Adaptor 156 may be, for example, a Urolok Adaptor™ sold by Boston Scientific Corporation. Adaptor 156 may define a channel (not shown) extending axially through adaptor 156 and having a wiper seal (not shown) arranged therein. The wiper seal may be comprised of silicone or low durometer rubber material to prevent backflow of fluid from the subject's body. The wiper seal may include a small opening. In order to pass one or more of end effector 208, control member 206, and/or sheath 204 of medical device 200 through the wiper seal of adaptor 156, an introducer 158 may be inserted into the small opening of the wiper seal so as to expand the size (e.g., diameter) of the opening. Once introducer 158 is in place within the channel and small opening of the wiper seal of adaptor 156, the wiper seal contacts and seals around an external surface of introducer 158 to maintain a fluidic seal therebetween. Adaptor 156 may also include a supplemental line or tubing 148 extending from a T-connection 146 of adaptor 156. Tubing 148 may be fluidly coupled to one or more sources of irrigation and/or suction fluid. Accordingly, irrigation fluid (not shown) may be delivered (e.g., pumped) through working channel 110 via tubing 148 in addition to or in the place of first branch 154 of port coupling 150. An end of tubing 148 opposite T-connection 146 may include a stop cock 144. When tubing 148 is not in use, tubing 148 may be sealed via stop cock 144 to prevent leakage of fluid.

Introducer 158 may have a proximal end 160 and a distal end 162 and include an introducer channel 164 extending therebetween. In use, distal end 162 of introducer 158 may be inserted into adaptor 156 to open the wiper seal, as discussed above. Introducer 158 may be tapered such that a cross-sectional dimension (e.g., diameter) of introducer 158 adjacent proximal end 160 is different (e.g., larger) than a cross-sectional dimension of distal end 162 of introducer 158. That is, introducer 158 may include a tapering or angled transition portion 166 between proximal end 160 and distal end 162 of introducer 158. As such, introducer channel 164 may narrow or taper distally along the length of introducer 158. Accordingly, end effector 208, control member 206, and/or sheath 204 may be guided or directed into working channel 110 through introducer 158. In the case of a basket or snare, tapered introducer channel 164 of introducer 158 may facilitate collapsing the basket or snare end effector 208 into working channel 110.

Handle 102 may also include a mounting bracket, clamp, or clip 170 for selectively coupling and uncoupling medical device 200 to handle 102. Clip 170 may include a pair of arms 172 and 174. Each of arms 172 and 174 may have a first end coupled to handle 102 in any appropriate manner such as, for example, glued, fastened, strapped, or any other such mechanical fastening (e.g., screws, pins, etc.) Alternatively, the first end of each of arms 172 and 174 may be monolithically formed as a one-piece construction with handle 102 via any appropriate process (e.g., molding). Additionally, each of arms 172 and 174 may have a second end, opposite the first end, which is free or otherwise uncoupled from handle 102. One or both of arms 172 and 174 may be semi-rigid, conformable, flexible, or resilient such that one or both arm 172 and 174 may pivot, flex, or deflect away from the other of arms 172 or 174 to increase a central holding space 176 between arms 172 and 174 upon the application of a force. Arms 172 and 174 may define opposed mating surfaces between which a handle 202 of medical device 200 may be securely held. In some arrangements, arms 172 and 174 may have a curved or arcuate profile or shape. Placement of handle 202 of medical device 200 in central holding area 176 between arms 172 and 174 may enable one-handed operation of medical system 100, as will be described in further detail below.

In addition to handle 202, medical device 200 may include sheath 204 and end effector 208 (e.g., a basket, snares, forceps, scissors, laser fibers, and/or needles) at a distal end of shaft or control member 206 (e.g., a wire, rod, hypotube, braid, shaft, and/or any other suitable drive member configured to transfer translational and/or rotational forces from its proximal end to its distal end). End effector 208 may be monolithically formed as a one-piece construction with control member 206 or a separate component coupled to control member 206 in any appropriate manner (e.g., gluing, heat staking, insert molding, etc.). At least a portion of end effector 208 may be movable relative to a sheath 204 and/or working channel 110 of shaft 104 between an extended state as shown in FIG. 1 and a retracted state (not shown), as will be described in further detail below. Further, in some arrangements, end effector 208 may be radially expandable and compressible. For example, end effector 208 may include a basket, graspers, or snare formed of shape-memory material such as, for example, Nitinol. As such, movement from the retracted state to the extended state may simultaneously cause movement of end effector 208 from a radially collapsed configuration (not shown) within sheath 204 to a radially expanded configuration external of sheath 204 as shown in FIG. 1. A working length of sheath 204 may be selected based on the manner of desired operation or holding by an operator. For example, in an arrangement in which medical device 200 is held in one hand while handle 102 is held in another, a working length of sheath 204 may be selected to enable sheath 204 to extend from handle 202 through introducer 158, through adaptor 156, through port coupling 150, and through working channel 110 to a position either flush with a distal-most end of shaft 104, or recessed or extended slightly relative to the distal-most end of shaft 104, while enabling sufficient slack for manipulation by the operator. In an arrangement in which handle 202 of medical device 200 is coupled to handle 102 via clip 170 (FIG. 3), as will be described in further detail below, the working length of sheath 204 may be reduced as less slack is required for manipulation by the operator. In an alternative arrangement, described below, medical device 200 may be directly coupled to port coupling 150 without the use of introducer 158 and adaptor 156. Accordingly, the working length of sheath 204 may be even further reduced. In any such arrangement, the length of control member 206 is selected based on the length of sheath 204.

Figure 2:
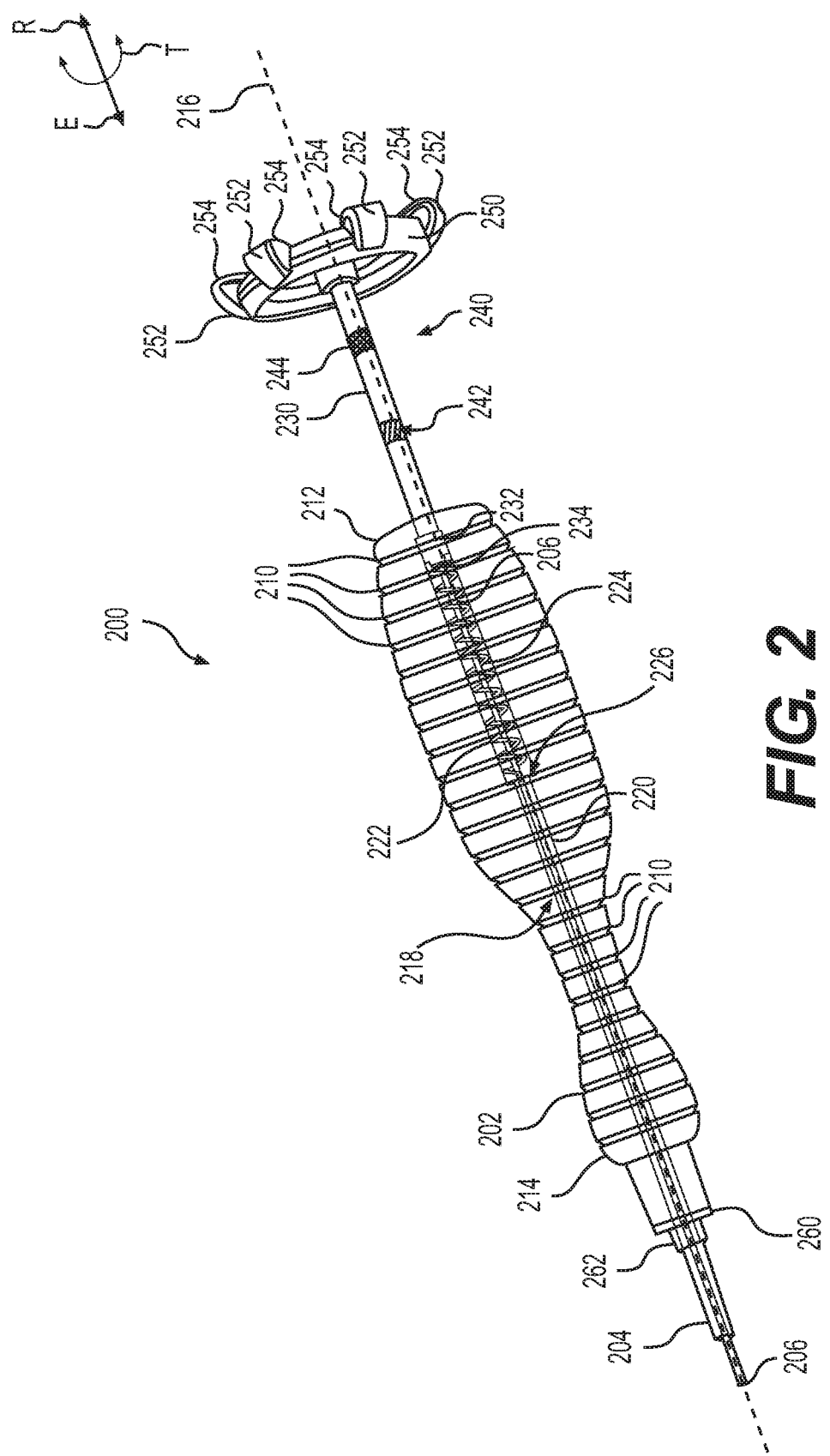
FIG. 2 illustrates a perspective view of the exemplary medical device of FIG. 1.

Referring to FIGS. 1 and 2, handle 202 of medical device 200 may be formed or comprised of any appropriate material such as molded polymers and/or the like. In some arrangements, handle 202 may be a molded polymer element having one or more circumferential, circular, or spiral (e.g., helical) cuts, incisions, and/or slots 210 extending into the thickness of handle 202. Such slots 210 may be continuous or discontinuous along the entire axial length of handle 202 between a proximal end 212 and a distal end 214 of handle 202, or along any portion thereof. Slots 210 may extend along a plane substantially perpendicular to a longitudinal axis 216 of handle 202. Alternatively, slots 210 may extend along a plane angled with respect to longitudinal axis 216 of handle 202. As used herein, the terms "about," "substantially," and "approximately," may indicate a range of values within +/−5% of a stated value. Slots 210 may be formed via any appropriate mechanism such as a knife, etc., and need not extend through the entire thickness of handle 210 at any given axial location. Slots 210 impart flexibility to handle 202. In use, an operator may grasp handle 202 in the palm of their hand, and due to slots 210, handle 202 may bend, conform, or otherwise deflect as appropriate to best fit the hand of the operator. For example, bending handle 202 may include moving proximal end 212 toward or away from distal end 214 about an axis normal to longitudinal axis 216. That is, bending handle may bring proximal end 212 toward distal end 214 by curving handle 202. As such, handle 202 ergonomically conforms to each operator's hand to enable comfortable control of medical device 200. In alternative arrangements, slots 210 are not present along handle 202. In such an arrangement, handle 202 may comprise a clam-shell arrangement in which two halves of handle 202 are coupled to one another to form handle 202.

Handle 202 may include a lumen 218 extending between proximal end 212 and distal end 214 of handle 202. Lumen may extend along central longitudinal axis 216 or may be positioned parallel to central longitudinal axis 216. Lumen 218 may include a first portion 220 and a second portion 222. As shown in FIG. 2, second portion 222 may have a cross-sectional dimension (e.g., diameter) larger than a cross-sectional dimension (e.g., diameter) of first portion 220. A spring 224 may be received within second portion 222. As such, second portion 222 may comprise a spring chamber. A flange 226 positioned between first portion 220 and second portion 222 may abut a distal end of spring 224. As such, flange 226 may act as a distal stop for spring 224. In some arrangements, the distal end of spring 224 may be fixed to flange 224.

A plunger 230 may be moveably received within second portion 222. For example, as shown in FIG. 2, a distal end 232 of plunger 230 may be received and slideable or otherwise moveable along central longitudinal axis 216 of handle 202 so as to selectively compress spring 224. Distal end 232 may define a seat 234 and a proximal end of spring 224 may abut seat 234 while enabling relative (e.g., rotational) movement between seat 234 and spring 224. As such, seat 234 may act as a proximal stop for spring 224. Control member 206 of medical device 200 may extend through first portion 220 and second portion 222 and be coupled to plunger 230. For example, as shown, control member 206 may extend through a central passage or opening through spring 224. A proximal end of control member 206 may be fixedly (e.g., heat staked, glued, stapled, insert molding, etc.) coupled to a portion of plunger 230 for movement therewith. That is, axial advancement, retraction, and rotation of plunger 230 relative to central longitudinal axis 216 causes likewise advancement, retraction, and rotation of control member 206, and consequently, end effector 204, as will be described in further detail below.

Plunger 230 may further include indicia 240 of a size of material (e.g., stone) to be removed from the body of the subject and the degree of plunger 230 stroke. Indicia 240 may include a first marker band 242 and a second marker band 244. Marker band 242 may have different characteristics (e.g., size, color, pattern, shape, and/or texture) than marker band 244. Accordingly, an operator may differentiate between marker band 242 and marker band 244 to ascertain a size of the material (e.g., stone) to be removed from the subject, and to gauge the extend of the stroke of the plunger 230, as will be described in further detail below. A proximal end of plunger 230 may be coupled to (or monolithically formed with) a grip, flange, wheel, or knob 250 in any appropriate manner (e.g., glued, screw connection, welded, heat staked, etc.). Knob 250 may include a surface enlarged relative a remainder of plunger 230 and facilitate placement of an operator's digit thereon for manipulation of medical device 200, as will be described in further detail below. For example, knob 250 may include a disc, ring, or wheel, for example, extending along an axis normal to longitudinal axis 216. Knob 250 may include a plurality of grips 252 thereon. As shown, grips 252 may be equally spaced (e.g., spaced at regular and consistent radial increments) about a circumferential surface of knob 250 and as such, may be indicative of a consistent angle of rotation of plunger 230, and consequently, control member 206 and end effector 208. In other arrangements, grips 252 may be not be equally spaced about the circumferential surface of knob 250. Grips 252 may have any appropriate shape. As shown, for example, grips 252 may be define a raised surface 254 relative to a proximal end of knob 250.

The handle 202 may include a proximal male medical (e.g., threaded) or slip luer 260. Luer 260 may be coupled to a corresponding female medical or slip luer 262, which is in turn, fixedly coupled (e.g., via adhesives, etc.) to sheath 204. Accordingly, sheath 204 may be securely fixed to handle 202 via the interaction between male luer 260 and female luer 262. The male luer 260 may optionally include a wiper seal (not shown) to prevent leakage of fluid when irrigating and/or aspirating through working channel 110. It is understood that in arrangements using adaptor 156, such an additional wiper seal may not be necessary.

In use, an operator may deliver an access sheath (not shown) through an opening of the subject and position a distal end of the access sheath at a location within the subject. Once in place, the operator may deliver shaft 104 through a lumen of the access sheath and insert medical device 200 through working channel 110. As shown in FIGS. 1 and 2, an operator may hold handle 102 in the palm of his or her left hand 304 and may hold handle 202 in the palm of his or her right hand 302 while placing one of his or her right digits (e.g., thumb 310) on knob 250. While the following description details the use of the medical system 100 with handle 202 of medical device 200 in the operator's right hand 302 and the handle 102 in the operator's left hand 304, such description is merely explanatory and the manner of gripping handles 102 and 202 may be reversed according to the operator's preferences.

With the handle 202 of medical device 200 in the operator's right hand 302, he/she may control all operation of end effector 208 via a single hand. That is, he or she can apply a force to push, urge advance, or otherwise depress plunger 230 in the direction E, against the bias of spring 224, so as to move end effector 208 towards the extended state distally of shaft 104 and sheath 204, and radially expanded state in the case of an expandable end effector 208, as shown in FIG. 1. Second marker band 244 may indicate the full stroke or full extension of end effector 208. That is, the operator may depress plunger 230 in the direction E until the second marker band 244 enters second portion 222 and is no longer visible to the operator, thereby indicting the maximum extension of end effector 208 relative to sheath 204 and/or working channel 110. Due to spring 224, removal of the force on the plunger 230, may cause plunger 230 to retract in the direction R as shown in FIG. 1. Such a retraction may transition end effector 208 from the extended (and optionally, expanded) state towards the retracted (and optionally, radially compressed) state (not shown). It is understood that the restoring force of spring 224 may be selected to adjust stress and strain imparted to a distal end of sheath 204 during material removal or other such procedures, and to adjust the force required by the operator to transition end effector 208 between the retracted state and the extended state. The restoring force may be calculated or approximated via Hooke's Law. In some alternative arrangements, spring 224 may be omitted. Rather, plunger 230, and therefore end effector 208, do not automatically return to the retracted stated. Rather, an operator must manually retract or pull plunger 230 in the direction R so as to move end effector 208 from the extended state to the retracted state.

In addition to movement of end effector 208 between the extended and retracted states, operator may rotate knob 250 in either the clockwise or counter-clockwise direction, as shown by arrow T, so as to rotate or turn end effector 208. It is understood that end effector 208 may be simultaneously extended and rotated, or simultaneously retracted and rotated.

The ability to simultaneously extend and rotate or retract and rotate enables the operator to employ a "spin scoop" or "spin drop" action in which, when end effector 208 (e.g., a basket) is in the extended state as shown in FIG. 1, and when end effector 208 is positioned against or in contact with a tissue or material (e.g., a stone), rotation of end effector 208 will cause one or more portions of the end effector (e.g., basket wire legs) to spread apart to catch the material in end effector 208. That is, the operator may extend end effector 208 distally in the direction E and push, direct, or otherwise guide a portion of end effector 208 into contact with tissue (e.g., a tissue wall, organ wall, body lumen, etc.) within the body of the subject. When end effector 208, which may include a basket having legs, is in contact with such tissue, the operator may rotate end effector 208 by turning knob 250. Due to the contact between at least a portion of end effector 208 and such tissue, rotation of end effector may cause a portion (e.g., a first leg) of end effector 208 to spread apart from another portion (e.g., a second leg) to create a widened opening or space between the first leg and the second leg. The widened space between the first leg and second leg may allow a stone or other such material to enter end effector 208 for retrieval. In a similar manner, any captured material may be released from end effector 208 by depressing plunger 230 such that end effector 208 is positioned against tissue and rotating plunger 230 to spread apart one or more portions of end effector 208 (e.g., basket wire legs) to release or drop captured material (e.g., a stone). That is, when end effector 208, which may include a basket having legs, is in contact with tissue, the operator may rotate end effector 208 by turning knob 250. Due to the contact between at least a portion of end effector 208 and such tissue, rotation of end effector 208 may cause a portion (e.g., a first leg) of end effector 208 to spread apart from another portion (e.g., a second leg) to create a widened opening or space between the first leg and the second leg. The widened space between the first leg and second leg may allow a stone or other such material previously contained within end effector 208 to be released.

When capturing a stone or other such material having a dimension (e.g., diameter, size) larger than the dimension (e.g., diameter, size) of working channel 110 and/or a dimension larger than a dimension of sheath 204, the restoring force of spring 224 retracts end effector 208 towards the retracted state and retains the stone or other material against a distal-most end of shaft 104 or sheath 204. First marker band 242 may be indicative of a size of the captured stone or material relative to the working channel 110 of shaft 104 or the sheath 204. For example, upon release of the operator's thumb 310 from knob 250, if first marker band 242 remains visible and is external of second portion 222, the captured stone or material is small enough to pass through the access sheath for removal. If, however, following release of the operator's thumb 310 from knob 250 first marker band 242 is not visible but is instead positioned in second portion 222 of handle 202, the captured stone or other material is too large to be passed through the access sheath without fragmentation (e.g., lithotripsy).

Figure 3:
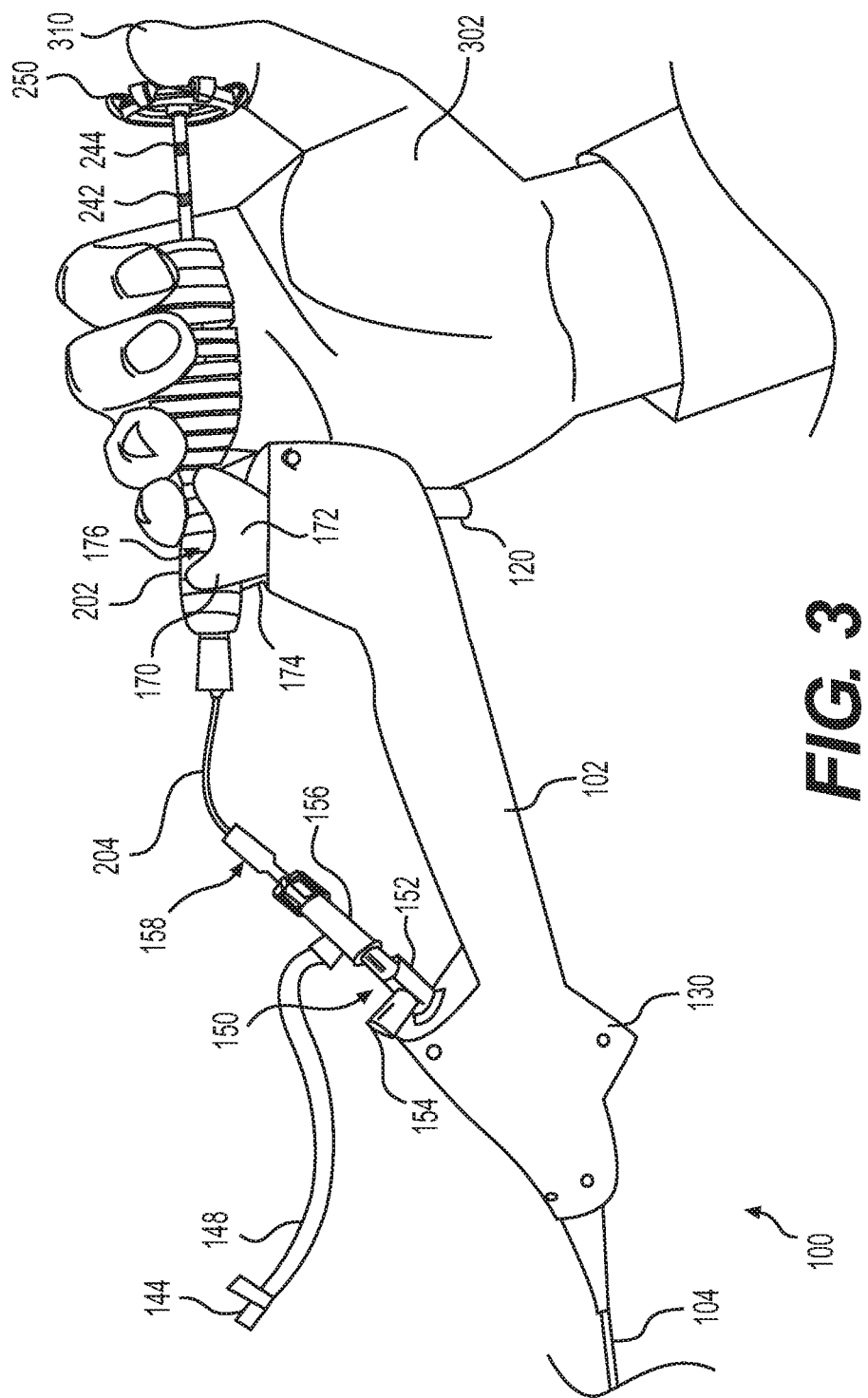
FIG. 3 illustrates the medical system of FIG. 1 arranged for one-handed operation.

Accordingly, an operator can extend, retract, and rotate end effector 208 through the manipulation of plunger 230 via their thumb 310, while holding handle 102 in their other hand. As such, a single operator may complete an entire medical procedure without an assistant, if so desired. In another arrangement, as shown in FIG. 3, medical device 200 may be coupled to handle 102 of medical system 100 to enable both handle 102 and handle 202 to be operated by a single hand of an operator. As shown in FIG. 3, handle 202 of medical device 200 may be coupled to handle 102 of medical system 100 via clip 170. Handle 202 may be received within central holding space 176 between the arms 172 and 174 to securely retain handle 202 therein. As such, an operator may hold both handle 102 and handle 202 in a single hand such as right hand 302. Medical device 200 may be actuated in the same manner as described above, via thumb 310 on knob 250. As noted above, a working length of sheath 204 and control member 206 may be selected to remove any unnecessary slack or the slack may be physically adjusted to selectively position end effector 208. By coupling handle 202 to handle 102, the operator's other hand, e.g., their left hand 304 is free to perform other functions such as, for example, insertion of an additional tool through working channel 110, manipulation of handle 102 or shaft 104 relative to an access sheath, to hold one or more portions of the subject's body, and/or to actuate or discontinue irrigation or aspiration fluids.

As noted above, in an alternative arrangement, medical device 200 may be directly coupled to port coupling 150 without the use of introducer 158 and adaptor 156. In such an arrangement, the working length of sheath 204 may be even further reduced relative to the arrangements of FIGS. 1 and 3. In such an arrangement, male luer 260 of medical device 200, having a wiper seal therein, may be directly coupled to female luer port coupling 150. Optionally, extension and retraction of end effector 208 of medical device 200 may be controlled via the degree of seating (e.g., threading) between male luer 260 and the female luer of port coupling 150. That is, when male luer 260 is not fully seated or threaded onto the female luer of port coupling 150, a distal end of sheath 204 and/or end effector 208 may not extend distally of shaft 104, and when male luer 260 is fully seated or threaded onto the female luer of port coupling 150, distal end of sheath 204 and/or end effector 208 may extend distally of shaft 104.

Additionally, in any arrangement discussed above, medical device 200 may be a "sheathless" or "sheath-free" medical device 200. A sheath-free medical device does not include a sheath 204, sleeve, or other such restraining member positioned about control member 206 and end effector 208. As such, expandable or otherwise actuatable portions of medical device 200 (e.g., end effector 208), if any, may freely expand toward an interior circumferential wall of working channel 110 within a shaft 104, while medical device 200 is positioned in the retracted state. Accordingly, rather than movement of end effector 208 relative to sheath 204 to move end effector 208 between the extended (and optionally radially expanded) and retracted (and optionally radially compressed) states, end effector 208 of medical device 200 moves between the extended (and optionally radially expanded) and retracted (and optionally radially compressed) states due to interaction between end effector 208 and working channel 110.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical system, comprising:
an insertion device having:
  a handle; and
  a port positioned on the handle of the insertion device and in fluid communication with a working channel of a shaft;
a medical device having:
  a control member terminating in an end effector;
  a handle having at least one slot positioned along the length of the handle, wherein at least a portion of the handle of the medical device is deflectable relative to another portion of the handle of the medical device via the at least one slot such that a proximal end of the handle is movable toward or away from a distal end of the handle about an axis normal to a longitudinal axis of the handle; and
  a plunger moveable along the longitudinal axis of the handle of the medical device.

2. The medical system of claim 1, wherein the plunger is rotatable about the longitudinal axis of the handle of the medical device.

3. The medical system of claim 1, wherein the plunger includes a plurality of indicia.

4. The medical system of claim 1, wherein the at least one slot is angled with respect to the longitudinal axis of the handle of the medical device.

5. The medical system of claim 1, wherein the at least one slot comprises at least one helical slot.

6. The medical system of claim 1, wherein the at least one slot comprises a circumferential or circular slot.

7. The medical system of claim 1, wherein the at least one slot includes an incision extending through a thickness of a wall of the handle of the medical device.

8. The medical system of claim 1, wherein the at least one slot includes a plurality of slots, and wherein at least some of the plurality of slots are discontinuous along a length of the handle of the medical device.

9. The medical system of claim 1, wherein the handle of the insertion device includes a clip on a proximal end thereof, the clip including a plurality of deflectable arms defining a receiving space therebetween.

10. The medical system of claim 9, wherein, in a coupled configuration, the handle of the medical device is positioned within the receiving space of the clip.

11. The medical system of claim 10, wherein, in the coupled configuration, the medical system is configured for one-handed operation.

12. A medical system, comprising:
an insertion device having:
  a handle;
  a port positioned on the handle of the insertion device and in fluid communication with a working channel of a shaft; and
  a coupling structure arranged proximally of the port on a proximal portion of the handle;
a medical device having:
  a control member terminating in an end effector;
  a handle having a plurality of slots along the length of the handle, wherein at least a portion of the handle of the medical device is deflectable relative to another portion of the handle of the medical device via one or more of the plurality of slots; and
  a plunger moveable along a longitudinal axis of the handle of the medical device;
wherein, in a coupled configuration, the handle of the medical device is coupled to the insertion device via the coupling structure.

13. The medical system of claim 12, wherein, in the coupled configuration, the medical system is configured for one-handed operation.

14. The medical system of claim 12, wherein the coupling structure includes one of a mounting bracket, clamp, or clip.

15. The medical system of claim 12, wherein the coupling structure includes a pair of deflectable arms, each arm of the pair of deflectable arms defining a mating surface for contact with the handle of the medical device.

16. The medical system of claim 12, wherein each of the plurality of slots is angled with respect to the longitudinal axis of the handle of the medical device.

17. The medical system of claim 12, wherein the handle of the medical device includes a channel extending along the longitudinal axis, wherein a distal end of the plunger is slidably positioned within a portion of the channel, and wherein the distal end of the plunger is rotatable with respect to the portion of the channel about the longitudinal axis of the handle of the medical device.

18. A medical system, comprising:
an insertion device having:
  a handle;
  a port positioned on the handle of the insertion device and in fluid communication with a working channel of a shaft; and
  a coupling structure arranged proximally of the port on a proximal portion of the handle;
a medical device having:
  a control member terminating in an end effector;
  a handle having a plurality of slots along the length of the handle, wherein at least a portion of the handle of the medical device is deflectable relative to another portion of the handle of the medical device via one or more of the plurality of slots such that a proximal end of the handle is movable toward or away from a distal end of the handle about an axis normal to a longitudinal axis of the handle, wherein the plurality of slots includes at least one of a circumferential slot, a helical slot, or circular slot; and
  a plunger moveable along the longitudinal axis of the handle of the medical device;
wherein, in a coupled configuration, the medical system is configured for one-handed operation.

19. The medical system of claim 18, wherein the coupling structure includes one of a mounting bracket, clamp, or clip.

20. The medical system of claim 18, wherein the coupling structure includes a pair of deflectable arms, each arm of the pair of deflectable arms defining a mating surface for contact with the handle of the medical device.

* * * * *